US00PP36671P2

(12) United States Plant Patent
Ranney et al.

(10) Patent No.: US PP36,671 P2
(45) Date of Patent: May 13, 2025

(54) ***ILEX* PLANT NAMED 'NCIC1'**

(50) Latin Name: *Ilex crenata*
Varietal Denomination: NCIC1

(71) Applicant: North Carolina State University, Raleigh, NC (US)

(72) Inventors: Thomas Green Ranney, Arden, NC (US); Irene Palmer, Arden, NC (US); Nathan Lynch, Arden, NC (US); Andra Windorf Nus, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 18/745,794

(22) Filed: Jun. 17, 2024

(51) Int. Cl.
*A01H 5/12* (2018.01)
*A01H 6/00* (2018.01)

(52) U.S. Cl.
USPC ..... Plt./247

(58) Field of Classification Search
USPC ..... Plt./247
CPC ..... A01H 5/12; A01H 5/00; A01H 6/00
See application file for complete search history.

(56) References Cited

PUBLICATIONS

ClickBid Mobile Bidding 2024, JC Raulston Arboretum at North Carolina State University Plant Sale retrieved on Sep. 9, 2024 at https://cbo.io/bidapp/index.php?slug=2024raulstonblooms, pp. 1-3, 19. (Year: 2024).*

* cited by examiner

*Primary Examiner* — June Hwu
(74) *Attorney, Agent, or Firm* — Cassandra Bright

(57) ABSTRACT

A new and distinct cultivar of *Ilex* plant named 'NCIC1' is disclosed, characterized by its compact, upright, rounded growth habit, and persistent, vivid yellow foliage. The new variety is an *Ilex*, normally produced as an outdoor garden or container plant.

2 Drawing Sheets

Latin name of the genus and species: *Ilex crenata*.
Variety denomination: 'NCIC1'.

BACKGROUND OF THE INVENTION

The present invention comprises a new and distinct *Ilex crenata* cultivar hereinafter referred to by the cultivar name 'NCIC1'. This new *Ilex crenata* was developed through a breeding program at a research nursery, located in Mills River, North Carolina. The intent of the breeding program was to develop *Ilex* varieties with persistent, vivid yellow foliage and a compact plant habit. 'NCIC1' was selected from an F2 population resulting from the parentage *Ilex crenata* 'Drops of Gold', U.S. Plant Pat. No. 14,420, and *Ilex crenata* 'Sky Pencil', unpatented, and *Ilex crenata* 'Golden Gem', unpatented. The direct parents (F1 generation of the breeding program) are unnamed and unpatented. The crossing resulting in the new variety was made in 2013. *Ilexcrenata* 'NCIC1' was found and selected as an interesting new cultivar in 2014 at the same nursery in Mills River, North Carolina.

The first asexual propagation of 'NCIC1' occurred in July 2016 by rooting stem cuttings at the same research nursery in Mills River, North Carolina. 'NCIC1' roots readily from softwood cuttings treated with a basal dip of 3,000-5,000 ppm indole butyric acid (potassium salt) in water. 'NCIC1' was repeatedly reproduced by vegetative cuttings over a seven-year period and has been found to retain its distinctive characteristics through successive asexual propagations.

Date of first public exposure was Jun. 27, 2023, in the United States. This was made directly by the inventor or one who obtained the claimed invention directly or indirectly from the inventor. This sale and all public disclosures made between Jun. 27, 2023, and the filing of this application fall within the exception allowed under 102(b)(1).

SUMMARY OF THE INVENTION

'NCIC1' has not been observed under all possible environmental conditions. The phenotype may vary somewhat with changes in light, temperature, soil and rainfall without, however, any variance in genotype.

The following traits have been observed and represent the characteristics of the new cultivar. In combination, these characteristics distinguish 'NCIC1' from all other varieties in commerce known to the inventor:

1. Persistent, vivid yellow foliage.
2. Compact, upright/rounded habit.

PARENT COMPARISONS

Table 1 compares typical characteristics of the new variety with the parent varieties.

TABLE 1

| Cultivar | Habit | Foliage color | Mature height | Mature width | Sex |
|---|---|---|---|---|---|
| 'Drops of Gold' | Broad, rounded, spreading | Yellow in sun | 120 cm | 150 cm | Female |

TABLE 1-continued

| Cultivar | Habit | Foliage color | Mature height | Mature width | Sex |
|---|---|---|---|---|---|
| 'Sky Pencil' | Upright, narrow | Green | 240 cm | 60 to 90 cm | Female |
| 'Golden Gem' | Flat-topped mound | Yellow in sun | 60 cm | 90 cm | Male |
| 'NCIC1' | Compact, upright/ rounded habit | Yellow in sun | 90 cm | 90 cm | Female |

COMMERCIAL COMPARISONS

Plants of the new cultivar 'NCIC1' are comparable to the patented, commercial variety *Ilex* 'ANNYS1', U.S. Plant Pat. No. 26,997. The two *Ilex* varieties are similar in most horticultural characteristics; however, the new variety 'NCIC1' differs in the following:

1. Foliage of 'NCIC1' is more resistant to burning in sun than foliage of 'ANNYS1'.
2. Mature plants of 'NCIC1' are larger than mature plants of 'ANNYS1'.

BRIEF DESCRIPTION OF THE PHOTOGRAPHS

Foliage and form of 'NCIC1' are illustrated by the accompanying photographs. The colors shown are as true as can be reasonably obtained by conventional photographic procedures. Colors in the photographs may differ slightly from the color values cited in the detailed botanical description, which accurately describe the colors of the new *Ilex crenata* 'NCIC1'.

DETAILED BOTANICAL DESCRIPTION

Figure 1:
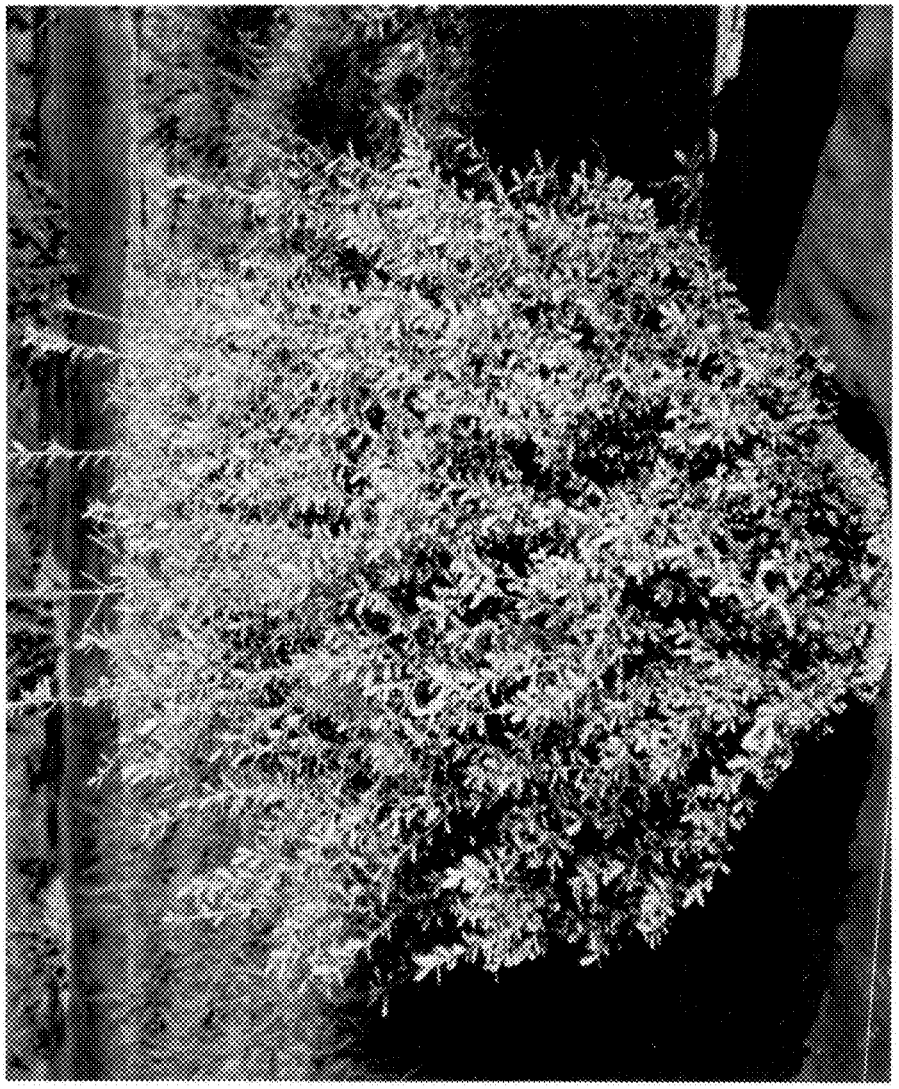
FIG. 1 is a photograph showing the habit of a four-year-old field-grown plant in fall of 2021, in Mills River, NC.
Figure 2:
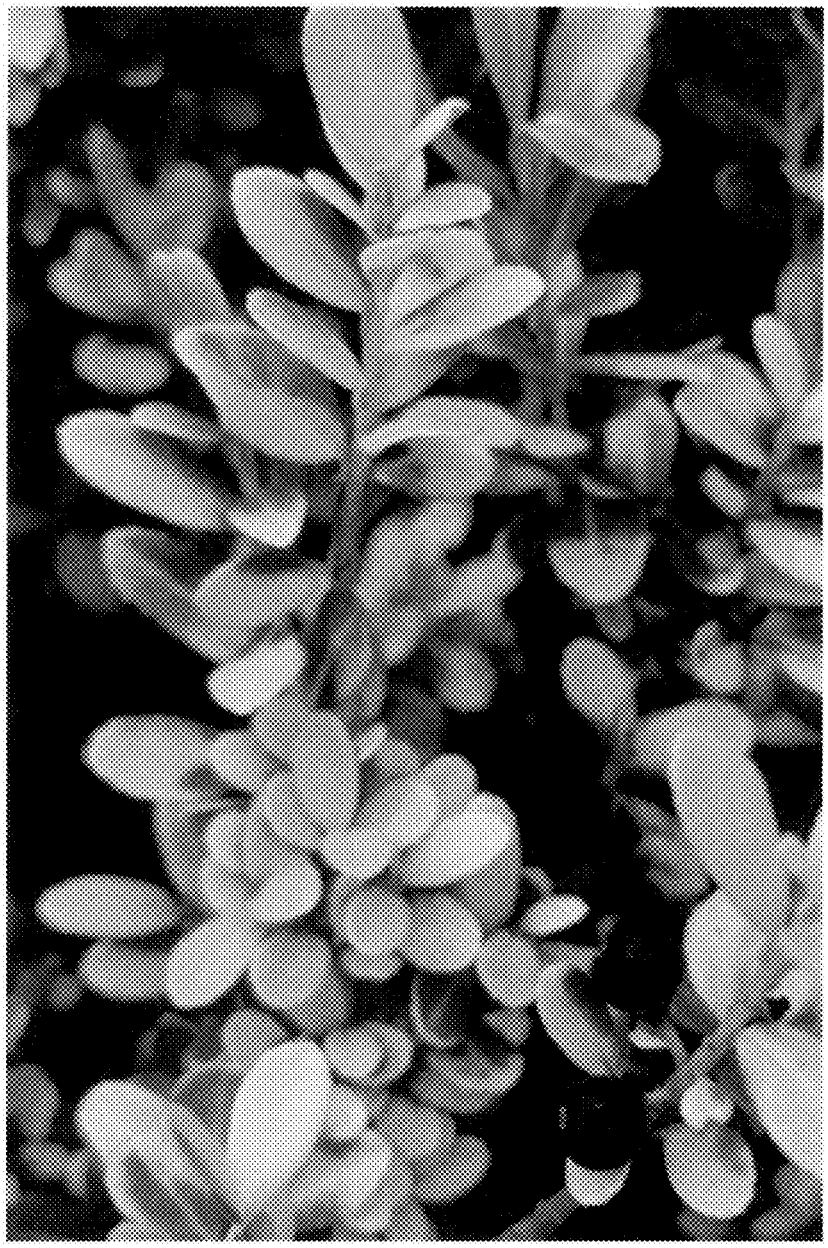
FIG. 2 is a photograph of the foliage of a ten-year old field-grown plant in fall of 2022, in Mills River, NC.

The following is a detailed description of the botanical characteristics of the new and distinct *Ilex crenata* 'NCIC1'. The detailed description was taken on a ten-year-old, field-grown plant in Mills River, North Carolina in fall 2022 and spring 2023. All colors cited herein refer to The Royal Horticultural Society Colour Chart (R.H.S.), London, Sixth Edition. Where specific dimensions, sizes, colors, and other characteristics are given, it is to be understood that such characteristics are approximations or averages set forth as accurately as practicable.

Botanical classification: *Ilex crenata* 'NCIC1'.

PROPAGATION

Type of propagation typically used: Softwood cuttings.
Time to initiate roots: 70 days in winter.
Number of days to produce a rooted plant: 95 days in winter.
Root description: Thin, fibrous, dense and freely-branched. Pale yellowish-brown to grey-brown in color, not accurately measured with R.H.S. chart.

PLANT

Type of plant: Evergreen shrub.
Age of plant described: 8 years old.
Growth habit: Compact, upright, rounded.
Height: 90 cm.
Plant spread: 90 cm.
Shoots (current year's growth):
- *Shoot length*.—Average 10 cm.
- *Shoot diameter*.—About 0.2 cm.
- *Color*.—RHS Yellow 15A mixed with Greyed-Orange 165B.
- *Texture*.—Finely pubescent.

Shoots (prior year's growth):
- *Stem length*.—Average 10 cm.
- *Stem diameter*.—About 0.4 cm.
- *Color*.—RHS Greyed-Green 197B.
- *Texture*.—Finely pubescent.

Branches (woody branches 2-4 years old):
- *Branch length*.—Average 31.1 cm.
- *Branch diameter*.—Average 0.8 cm.
- *Color*.—RHS Greyed-Green RHS 197B.
- *Texture*.—Glabrous with vertical fissures.

Internode length: Average 0.3 cm.

FOLIAGE

Leaf:
- *Arrangement*.—Alternate, simple.
- *Average length*.—2.2 cm.
- *Average width*.—0.9 cm.
- *Shape of blade*.—Elliptical.
- *Apex*.—Acute.
- *Base*.—Cuneate.
- *Margin*.—Serrulate.
- *Texture of top surface*.—Glabrous, coriaceous.
- *Texture of bottom surface*.—Glabrous, coriaceous.
- *Color*.—Young foliage upper side: RHS Greyed-Orange 164A. Young foliage under side: Near RHS Greyed-Orange 164C. Mature, inner shaded foliage upper side: RHS Green 139A. Mature, inner shaded foliage under side: RHS Green 137B. Mature, outer foliage in sun upper side: RHS Yellow 15A when completely yellow; otherwise Yellow 15A mottled with Green 139A. Mature, outer foliage in sun under side: RHS Yellow 11A.
- *Venation*.—Type: Pinnate. Color, mature outer foliage in sun, upper and under sides: RHS Yellow 11A. Color, mature inner shaded foliage, upper and under sides: RHS Yellow-Green 145A.
- *Petiole*.—Length: About 0.2 cm. Diameter: Less than 0.1 cm. Color: Outer foliage in sun: RHS Yellow 11A. Inner shaded foliage: RHS Yellow-Green 145A. Texture: Finely pubescent.

FLOWER

Natural flowering season: May to June in Mills River, North Carolina.
Inflorescence type: Solitary female flowers in the leaf axils.
Quantity of flowers: 1 per inflorescence.
Flowers:
- *Height*.—About 0.3 cm.
- *Diameter*.—About 0.5 cm.

Petals:
- *Quantity*.—4 per flower.
- *Shape*.—Ovate.
- *Margin*.—Entire.
- *Texture*.—Smooth, both upper and lower surfaces.
- *Length*.—About 0.4 cm.

*Width*.—About 0.3 cm.
*Apex*.—Rounded.
*Base*.—Cuneate.
*Color*.—RHS Green-White 157D, both upper and lower surfaces.

Peduncle:
*Length*.—About 0.5 cm.
*Diameter*.—Less than 0.1 cm.
*Texture*.—Glabrous.
*Color*.—RHS Yellow-Green 144A.

REPRODUCTIVE ORGANS

Gynoecium:
Pistil:
*Number*.—1 per flower.
*Length*.—Approximately 2 mm.
*Style length*.—About 1 mm.
*Stigma shape*.—Flattened.
*Ovary shape*.—Round.
*Ovary length*.—About 1 mm.

FRUIT AND SEED

Fruit:
*Type*.—Berry-like drupe.
*Shape*.—Round.
*Length*.—About 0.5 cm.
*Width*.—About 0.5 cm.
*Color*.—RHS Black 203B.
*Texture*.—Glabrous.

Seed:
*Number*.—1 to 3 per fruit.
*Length*.—About 0.4 cm.
*Width*.—About 0.3 cm.
*Color*.—RHS Brown N200C.
*Texture*.—Glabrous.

OTHER CHARACTERISTICS

Temperature tolerance: At least USDA zone 6b; testing has not been completed in colder zones.

Disease/pest resistance: No significant disease or insect pests have been observed.

What is claimed is:

1. A new and distinct cultivar of *Ilex crenata* plant named 'NCIC1' as illustrated and described herein.

* * * * *